(12) United States Patent
Kim

(10) Patent No.: US 7,183,345 B2
(45) Date of Patent: Feb. 27, 2007

(54) SUPERABSORBENT CARBOXYL-CONTAINING POLYMERS WITH ODOR CONTROL PROPERTIES AND METHOD FOR PREPARATION

(75) Inventor: Young-Sam Kim, Midland, MI (US)

(73) Assignee: Stockhausen GmbH, Krefeld (DE)

( * ) Notice: Subject to any disclaimer, the term of this patent is extended or adjusted under 35 U.S.C. 154(b) by 279 days.

(21) Appl. No.: 10/471,874

(22) PCT Filed: Jun. 26, 2002

(86) PCT No.: PCT/US02/20872

§ 371 (c)(1),
(2), (4) Date: Mar. 25, 2004

(87) PCT Pub. No.: WO03/002089

PCT Pub. Date: Jun. 9, 2003

(65) Prior Publication Data

US 2004/0157971 A1    Aug. 12, 2004

Related U.S. Application Data

(60) Provisional application No. 60/302,328, filed on Jun. 29, 2001.

(51) Int. Cl.
*C08K 3/10* (2006.01)
(52) U.S. Cl. .................. 524/403; 524/444; 524/556
(58) Field of Classification Search ................ 524/403, 524/444, 556
See application file for complete search history.

(56) References Cited

U.S. PATENT DOCUMENTS

| | | | |
|---|---|---|---|
| 4,286,082 A | 8/1981 | Tsubakimoto et al. ...... 526/240 |
| 4,295,987 A | 10/1981 | Parks ......................... 252/194 |
| 4,303,771 A | 12/1981 | Wagner et al. ............... 526/125 |
| 4,340,706 A | 7/1982 | Obayashi et al. ........... 526/207 |
| 4,385,632 A | 5/1983 | Odelhög ..................... 604/360 |
| 4,506,052 A | 3/1985 | Furukawa et al. .......... 524/357 |
| 4,610,678 A | 9/1986 | Weisman et al. ........... 604/368 |
| 4,654,039 A | 3/1987 | Brandt et al. ............... 604/368 |
| 4,666,983 A | 5/1987 | Tsubakimoto et al. ...... 525/119 |
| 4,734,478 A | 3/1988 | Tsubakimoto et al. ...... 527/300 |
| RE32,649 E | 4/1988 | Brandt et al. ............... 604/368 |
| 4,962,172 A | 10/1990 | Allen et al. ............. 526/318.42 |
| 5,002,986 A * | 3/1991 | Fujiura et al. ................. 524/47 |
| 5,145,906 A | 9/1992 | Chambers et al. .......... 524/732 |
| 5,147,956 A | 9/1992 | Allen ..................... 526/318.42 |
| 5,342,899 A | 8/1994 | Graham et al. ............. 525/301 |
| 5,506,324 A | 4/1996 | Gartner et al. ......... 526/318.41 |
| 5,629,377 A * | 5/1997 | Burgert et al. .............. 524/832 |
| 5,744,564 A | 4/1998 | Stanley, Jr. et al. ...... 526/317.1 |
| 5,994,440 A | 11/1999 | Staples et al. .............. 524/377 |
| 6,096,299 A | 8/2000 | Guarracino et al. ....... 424/76.1 |
| 6,277,772 B1 * | 8/2001 | Gancet et al. .............. 442/327 |
| 6,468,521 B1 * | 10/2002 | Pedersen et al. ......... 424/78.17 |
| 6,716,895 B1 * | 4/2004 | Terry ........................... 523/122 |
| 6,726,936 B1 * | 4/2004 | Asano et al. ............... 424/618 |
| 2004/0138362 A1 * | 7/2004 | Kim ........................... 524/403 |

FOREIGN PATENT DOCUMENTS

| | | |
|---|---|---|
| EP | 392608 | 6/1995 |
| GB | 2119384 | 11/1983 |
| JP | 05179053 | 7/1993 |
| WO | WO 9965317 A1 * | 12/1999 |
| WO | WO0009173 A * | 2/2000 |

OTHER PUBLICATIONS

Derwent Abstract 1978-60669A, German Patent 2706135, E. Barthell, et al., Sep. 1, 1993.
U.S. Appl. No. 10/480,328; Young-Sam; Superabsorbent Carboxyl-Containing Polymers With Odor Control Properties And Method For Preparation., Jun. 26, 2002.
U.S. Appl. No. 10/469,664; Young-Sam; Water-Absorbent Carboxyl-Containing Polymers With Low Monomer Content, Jun. 26, 2002.

* cited by examiner

*Primary Examiner*—David W. Wu
*Assistant Examiner*—Satya Sastri
(74) *Attorney, Agent, or Firm*—Smith Moore LLP

(57) ABSTRACT

This invention relates to a water-absorbent, water insoluble polymer comprising silver complex ions.

8 Claims, No Drawings

SUPERABSORBENT CARBOXYL-CONTAINING POLYMERS WITH ODOR CONTROL PROPERTIES AND METHOD FOR PREPARATION

CROSS REFERENCE TO RELATED APPLICATIONS

This application is a 371 of PCT/US02/20872 filed Jun. 26, 2002, which claims the benefit of U.S. Provisional Application Ser. No. 60/302,328, filed Jun. 29, 2001.

BACKGROUND OF THE INVENTION

This invention relates to superabsorbent polymers with odor control properties.

Water-absorbent polymers, also referred to as superabsorbent polymers or aqueous fluid absorbent polymers, are primarily used in personal care products which absorb body fluids, for example, baby diapers, adult incontinence products and feminine hygiene products. In such applications, superabsorbent polymer particles are incorporated into absorbent structures that contain synthetic and/or natural fiber or paper based, woven and nonwoven structures, or toughened masses of fibers, such as fluff pads. The materials used in such structures can quickly absorb aqueous fluids and distribute them throughout the whole absorbent structure. The structures, in the absence of superabsorbent polymers, have limited absorption capacity, are bulky due to the large amount of material needed to provide acceptable absorption capacity, and do not retain fluid under pressure. A means for improving the absorbency and fluid retention characteristics of such absorbent structures is to incorporate superabsorbent polymer particles which imbibe fluids to form a swollen hydrogel material.

The superabsorbent polymer particles quickly absorb fluids and retain such fluids to prevent leakage and give the absorbent structure a "dry feel" even when wetted. See U.S. Pat. No. 4,610,678 for examples of such polymers. See also U.S. Pat. Nos. 4,654,039 and Re. 32,649, which disclose a process for the preparation of superabsorbent polymers and the use of known crosslinking agents for such polymers, and also U.S. Pat. Nos. 4,295,987 and 4,303,771. A variation of the basic process is taught in GB Patent 2,119,384, which discloses a post polymerization surface crosslinking process in which the previously polymerized absorbent polymer powder is mixed with crosslinkers, preferably polyalcohols, a solvent and water, to coat the polymer surface and is heated to temperatures in the range of 90 to 300° C. to crosslink the surface. U.S. Pat. No. 5,506,324 discloses superabsorbent polymer particles comprising polymers containing carboxyl moieties which are crosslinked using $C_{2-10}$ polyhydric hydrocarbons which are ethoxylated with from 2 to 8 ethylene oxide units per hydroxyl moiety of the polyhydric hydrocarbon wherein the hydroxyl moiety at the end of each ethylene oxide chain is esterified with a $C_{2-10}$ unsaturated carboxylic acid or ester thereof. In a preferred embodiment, the superabsorbent polymer particles are subjected to a heat-treatment process after drying and sizing the particles.

It would be desirable, especially for the use of superabsorbent polymers in feminine hygiene products and adult incontinence products, to have a superabsorbent polymer that reduces unpleasant odors that might develop in use, particularly when contacted with bacteria infected urine.

Different methods have been employed in the prior art to reduce malodor in superabsorbent polymer-containing devices.

Various odor-controlling agents are known in the prior art. Odors can be in general chemically classified as being basic, acidic and neutral. Odor-controlling agents can combat odors based on different mechanisms such as, for example, absorption, adsorption and inclusion complexation of malodor causing molecules, masking and modification of malodor causing molecules, inhibition of malodor producing microorganisms or a combination of these mechanisms.

European Patent Publication 392 608 discloses a disposable absorbent polymer product which comprises a cyclodextrin, especially β-cyclodextrin, and an active agent, for example, a perfume. WO 99/64485 also relates to superabsorbent polymers containing cyclodextrins. However, cyclodextrins are biologically degradable, and are a good nurture for microorganisms. When contacted with microorganisms, such as the bacteria in infected urine, bacteria proliferation is increased, resulting in increased malodor. Furthermore, cyclodextrins are often very fine dusty substances that are difficult to handle on a large commercial processing scale.

U.S. Pat. No. 4,385,632 is directed to an absorbent article for urine which contains a water-soluble copper salt, for example copper acetate, which impedes bacterial growth, prevents ammonia production and binds ammonia by complexation so as to prevent the occurrence of unpleasant odor. The copper ion treatment is less favorable not only due to its low efficacy even at relatively high concentrations in the case of heavy incontinence where severe urinary tract infection is present, but also due to coloring which may limit its use in hygiene articles from the aesthetic viewpoint.

U.S. Pat. No. 6,096,299 discloses an absorbent article containing an odor control material that comprises a zeolite having a particle size of more than 200 μm. The zeolite may optionally be mixed with a superabsorbent polymer and activated carbon. WO 98/20915 concerns a superabsorbent composition containing a superabsorbent polymer powder and a zeolite powder exchanged with metal cations having bactericidal properties, such as Ag, Cu and Zn ions. It is a disadvantage of zeolite materials that they are less effective in controlling odor when used in swollen superabsorbent polymer gels. It is assumed that the odor absorbing capacity, that is, the pores of the zeolite, may partially be filled by water molecules instead of volatile odor-causing molecules. Furthermore, zeolite materials are in general fine dusty substances that are difficult to handle on a large commercial scale.

Japanese Patent Publication 05179053 relates to a method for producing a water absorbent resin with good antimicrobial properties wherein the resin contains a water-insoluble inorganic phosphate compound, for example, silver sodium hydrogen zirconium phosphate (sold under the tradename Antimicrobial ALPHASAN RC 5000 by Milliken Chemicals, USA). The inorganic phosphate compound has a general formula of $M^1{}_aA_bM^2{}_c(PO_4)_d \cdot nH_2O$. $M^1$ is selected from Ag, Cu, Zn, Sn, Hg, Pb, Fe, Co, Ni, Mn, As, Sb, Bi, Ba, Cd and Cr. A is selected from alkali metal ions, alkaline earth metal ions, $NH_4$ and H, preferably, $M^1$ is, for example, Ag; A is, for example, Li, Na, $NH_4$ or H; $M^2$ is, for example, Zr, Ti or Sn. It is assumed that the $M^1$ ions captured in the network structure of the specified phosphate compound are released as in the case of heavy metal ion exchanged zeolites. However, these inorganic phosphate compounds have drawbacks similar to those of the zeolite materials mentioned above.

WO 00/78281 discloses an anti-microbial absorbent product comprising homogeneously dispersed particles of metallic silver having a particle size in the range of 1 to 50 nm. One embodiment relates to a disposable absorbent article comprising superabsorbent polymers. However, the preparation of the silver nano-particles is complicated.

As seen above, most existing methods are incapable of sufficiently reducing malodor, or have other drawbacks. They often require treatments with malodor adsorbents, or perfume/fragrance. The use of perfume/fragrance can mask the malodor but it can be difficult to match the personal odor preference of the user. Often, the offensiveness of the combination of malodor and perfume is perceived to be more than that of the malodor alone. The various treatments in the prior art involve complicated and time-consuming process steps and are also often detrimental with regard to the absorption capacity and other properties of the superabsorbent polymer. Therefore, it would be highly desirable to provide a superabsorbent polymer with odor control properties that is unaffected in its absorbency properties. It also would be desirable to develop a simple process for preparing the superabsorbent.

SUMMARY OF THE INVENTION

This invention relates to a water-absorbent, water insoluble polymer comprising silver complex ions.

A further aspect of the invention is a process for the preparation of a water-absorbent, water insoluble polymer, which comprises:
(I) polymerizing a polymerization mixture comprising:
  (a) one or more ethylenically unsaturated carboxyl-containing monomers,
  (b) one or more crosslinking agents,
  (c) optionally one or more comonomers copolymerizable with the carboxyl-containing monomer, and
  (d) a polymerization medium, to form a crosslinked hydrogel,
(II) comminuting the hydrogel to particles, and (II) drying the hydrogel, wherein a solution comprising silver complex ions is added in at least one of the following steps:
(i) to the polymerization mixture during polymerization or prior to the beginning of the polymerization, or (ii) to the crosslinked hydrogel prior to or after comminution in step (II), or (iii) to the dried polymer particles after step (III).

Another aspect of the invention is a superabsorbent polymer prepared by the process of the invention. This invention also concerns an absorbent structure comprising the superabsorbent polymer of this invention and at least one of a woven or nonwoven structure of paper, synthetic fibers, or natural fibers.

The superabsorbent polymer of this invention is very effective in preventing malodor that can develop when a polymer comes in contact with biological fluids such as urine or blood. It is known that microorganisms play an important role in the development of malodor. For example, bacteria strains that are capable of producing urease enzyme split the urea of the urine into ammonia and carbon dioxide. It is assumed that skin irritation, and the foul smell of urine, are mainly due to the production of ammonia by urea cleavage of urease from the bacteria in the urine and in the perineal region. Bacteria proliferation and ammonia production are significantly inhibited in a device comprising the superabsorbent polymers of the invention.

In principle, all metal ions may inactivate bacteria by reacting outside or inside bacteria cells to some extent, either directly or indirectly. Indeed, various metal ions have been long known and used as antibacterial agents. It has now been found that silver complex ions show surprisingly improved positive odor control versus other antibacterial metal ions that might be commercially acceptable to diaper producers, such as aluminum, copper, and zinc.

It is indeed surprising that the use of expensive and difficult to handle carriers like zeolites and specific insoluble inorganic phosphates is not necessary in combination with silver complex ions to provide effective odor control.

In addition, silver complex ions are more light resistant than any soluble silver salt. They do not affect the color negatively and are less likely to degrade the whiteness of the superabsorbent polymer. The silver complex ions in the present superabsorbent polymer may be either "free" complex ions or they may be included in a particulate porous carrier, such as a zeolite.

DETAILED DESCRIPTION OF THE INVENTION

The present invention combines silver complex ions with water-insoluble, water-absorbent polymers.

The silver complex ions are applied to the process as either an aqueous solution or as a solution in a mixture of water and organic solvent. Advantageously, the solution comprising silver complex ions is prepared in-situ by reacting a silver salt with a complexation agent. For example, a wide variety of soluble silver salts can be complexed by thiosulfate anions.

The solubility of various silver salts can be in general improved by acidifying, dissolving them in alkalis, dissolving them in organic solvent, dissolving them at elevated temperatures, and/or intensive mixing during the dissolution process. The degree of solubility of the silver salt is not particularly critical. Preferably, the soluble silver salts have a solubility of not less than 10 g per liter.

However, the preferred source of silver for preparation of the silver complex ions of the present invention are water-insoluble silver salts, which are virtually insoluble in pure water at ambient temperature. Preferably, water-insoluble silver salts have a $pK_s$ value of at most 50.3. More preferably, water-insoluble silver salts have a $pK_s$ value of at least 7.5 but at most 16.1, most preferably the $pK_s$ value is at least 9 but at most 13.

Exemplary complexation agents for the water-insoluble silver salts include ammonia, cyanide salts, chloride salts, bromide salts and thiosulfate salts. Preferred complexation agents are chloride and thiosulfate salts of alkali metals, alkaline earth metals or with ammonium cations, and more preferred complexation agents are thiosulfate salts of alkali metals, alkaline earth metals, or with ammonium cations. Representative thiosulfate salts are lithium thiosulfate, sodium thiosulfate, potassium thiosulfate, calcium thiosulfate, magnesium thiosulfate, barium thiosulfate and ammonium thiosulfate. The most preferred complexation is sodium thiosulfate and most preferably is used in the form of an aqueous solution.

In a preferred embodiment the ratio of silver cations to complexing anions in the solution comprising the silver complex ions is from 0.001 to 100. The aqueous solution of silver complex ions may be heterogeneous, that is, silver salts may be dissolved by incomplete complexation, based on the molar ratio of silver cations to complexing anions. The solubility and the speed of dissolution of water-insoluble silver salts during the in-situ preparation of silver complex ion solutions can be improved by using an excessive amount of complexing anions, elevating temperature or intense mixing in order to prepare an aqueous silver complex ion solution.

Examples of water-insoluble silver salts include silver bromide, silver carbonate, silver chloride, silver chromate, silver diethyldithiocarbamate, silver iodate, silver iodide, silver phosphate, and silver sulfide. The preferred water-insoluble silver salts are silver chloride and silver bromide, and the most preferred water-insoluble silver salt is silver chloride. Mixtures of silver salts can be employed.

The superabsorbent polymer preferably comprises silver cations in the silver complex ions in an amount of from 1 ppm to 100,000 ppm, more preferably from 1 to 10,000 ppm, even more preferably from 10 to 1,000 ppm and most preferably from 25 to 1,000 ppm, all based on the dry weight of the polymer. Preferably, amount of silver complex ion employed is at least 1 ppm, more preferably at least 10 ppm, and most preferably at least 25 ppm based on the weight of dry polymer. The amount of silver complex ion employed advantageously is at most 10,000 ppm, preferably at most 3,000 ppm, more preferably at most 1,000 ppm, and most preferably at most 500 ppm based on the weight of dry polymer.

The water-absorbent, water-insoluble polymers advantageously are derived from one or more ethylenically unsaturated carboxylic acids, ethylenically unsaturated carboxylic acid anhydrides or salts thereof. Additionally, the polymers may include comonomers known in the art for use in superabsorbent polymers or for grafting onto the superabsorbent polymers including comonomers such as an acrylamide, an acrylonitrile, a vinyl pyrrolidone, a vinyl sulphonic acid or a salt thereof, a cellulosic monomer, a modified cellulosic monomer, a polyvinyl alcohol or a starch hydrolyzate. If used, the comonomer comprises up to 25 percent by weight of the monomer mixture.

Preferred unsaturated carboxylic acid and carboxylic acid anhydride monomers include the acrylic acids typified by acrylic acid, methacrylic acid, ethacrylic acid, α-chloro-acrylic acid, α-cyano acrylic acid, β-methyl acrylic acid (crotonic acid), α-phenyl acrylic acid, β-acryloyloxy propionic acid, sorbic acid, α-chloro sorbic acid, angelic acid, cinnamic acid, p-chloro cinnamic acid, beta-styrenic acrylic acid (1-carboxy4-phenyl butadiene-1,3), itaconic acid, citraconic acid, mesaconic acid, glutaconic acid, maleic acid, fumaric acid and maleic acid anhydride. More preferably the starting monomer is acrylic acid, methacrylic acid, or a salt thereof with acrylic acid or a salt thereof being most preferred. The use herein of the prefix "(meth)" with generic terms, such as, for example, "acrylic acid", or "acrylate" is meant to broaden the terms to include both acrylate and methacrylate species. Thus, the term "(meth)acrylic acid monomer" includes acrylic acid and methacrylic acid.

Preferably, 25 mole percent or greater of the carboxylic acid units of the hydrophilic polymer are neutralized with base, even more preferably 50 percent or greater and most preferably 65 percent or greater. This neutralization may be performed after completion of the polymerization. In a preferred embodiment the starting monomer mix has carboxylic acid moieties that are neutralized to the desired level prior to polymerization.

The final polymer or the starting monomers may be neutralized by contacting them with a salt forming cation. Such salt-forming cations include alkaline metal ammonium, substituted ammonium and amine based cations. Preferably, the polymer is neutralized with an alkali metal hydroxide such as, for example, sodium hydroxide or potassium hydroxide, or an alkali metal carbonate such as, for example, sodium carbonate or potassium carbonate.

The water-absorbent polymers of the invention are lightly crosslinked to make them water-insoluble. Vinyl, non-vinyl, or dimodal crosslinkers can be employed, either alone, as mixtures, or in various combinations. Polyvinyl crosslinkers commonly known in the art for use in superabsorbent polymers advantageously are employed. Preferred compounds having at least two polymerizable double bonds include: di- or polyvinyl compounds such as divinyl benzene, divinyl toluene, divinyl xylene, divinyl ether, divinyl ketone and trivinyl benzene; di- or polyesters of unsaturated mono- or polycarboxylic acids with polyols, such as di- or tri-(meth)acrylic acid esters of polyols such as ethylene glycol, diethylene glycol, triethylene glycol, tetra ethylene glycol, propylene glycol, dipropylene glycol, tri propylene glycol, tetra propylene glycol, trimethylol propane, glycerin, polyoxyethylene glycols and polyoxypropylene glycols; unsaturated polyesters that can be obtained by reacting any of the above-mentioned polyols with an unsaturated acid such as maleic acid; di- or polyesters of unsaturated mono- or polycarboxylic acids with polyols derived from reaction of $C_2$–$C_{10}$ polyhydric alcohols with 2 to 8 $C_2$–$C_4$ alkylene oxide units per hydroxyl group, such as trimethylol propane hexaethoxyl triacrylate; di- or tri-(meth)acrylic acid esters that can be obtained by reacting polyepoxide with (meth) acrylic acid; bis(meth) acrylamides such as N,N-methylenebisacrylamide; carbamyl esters that can be obtained by reacting polyisocyanates such as tolylene diisocyanate, hexamethylene diisocyanate, 4,4'-diphenyl methane diisocyanate and NCO-containing prepolymers obtained by reacting such diisocyanates with active hydrogen atom-containing compounds with hydroxyl group-containing monomers, such as di-(meth)acrylic acid carbamyl esters obtainable by reacting the above-mentioned diisocyanates with hydroxyethyl(meth)acrylate; di- or poly(meth)allyl ethers of polyols such as alkylene glycols, glycerol, polyalkylene glycols, polyoxyalkylene polyols and carbohydrates such as polyethylene glycol diallyl ether, allylated starch, and allylated cellulose; di- or poly-allyl esters of polycarboxylic acids, such as diallyl phthalate and diallyl adipate; and esters of unsaturated mono- or polycarboxylic acids with mono (meth)allyl ester of polyols, such as allyl methacrylate or (meth)acrylic acid ester of polyethylene glycol monoallyl ether.

The preferred classes of crosslinkers include, for example, bis(meth)acrylamides; allyl(meth)acrylates; di- or poly-esters of (meth)acrylic acid with polyols such as diethylene glycol diacrylate, trimethylol propane triacrylate, and polyethylene glycol diacrylate; and di- or polyesters of unsaturated mono- or poly-carboxylic acids with polyols derived from the reaction of $C_1$–$C_{10}$ polyhydric alcohols with 2 to 8 $C_2$–$C_4$ alkylene oxide units per hydroxyl group, such as ethoxylated trimethylol propane triacrylate. More preferably the crosslinking agents correspond to Formula 1:

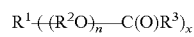　　　　　　　　　　　　　　　　　　Formula 1 wherein:
$R^1$ is a straight- or branched-chain polyalkoxy radical with 1 to 10 carbon atoms, optionally substituted with one or more oxygen atoms in the backbone, having x valences;
$R^2$ is independently in each occurrence an alkylene group of 2 to 4 carbon atoms;
$R^3$ is independently in each occurrence a straight- or branched-chain alkenyl moiety with 2 to 10 carbon atoms;
n is a number from 1 to 20; and x is a number from 2 to 8.

In the most preferred embodiment the polyvinyl crosslinker corresponds to Formula 1 wherein $R^1$ is derived from trimethylolpropane, $R^2$ is ethylene —$(CH_2CH_2)$—, $R^3$ is vinyl —$(CH=CH_2)$, the average value of n is from 2 to 6, and x is 3. The most preferred polyvinyl crosslinker is highly ethoxylated trimethylolpropane triacrylate, containing an average of 15 to 16 ethoxyl groups per molecule of trimethylolpropane. Crosslinkers corresponding to Formula 1 are available from Craynor under the trademark Craynor and from Sartomer under the trademark Sartomer. Generally, the crosslinkers described by Formula 1 are found as a mixture of materials described by the formula and by-products resulting from the preparation process. Mixtures of polyvinyl crosslinkers can be employed.

The non-vinyl crosslinkers of this invention are agents having at least two functional groups capable of reacting with the carboxyl groups of the polymer, and include materials such as glycerin, polyglycols, ethylene glycol digylcidyl ether, and diamines. Many examples of these agents are given in U.S. Pat. Nos. 4,666,983 and 4,734,478 which teach the application of such agents to the surface of absorbent polymer powder followed by heating to crosslink surface chains and improve absorption capacity and absorption rate. Additional examples are given in U.S. Pat. No. 5,145,906, which teaches post-crosslinking with such agents. In the current invention, the non-vinyl crosslinkers advantageously are added homogeneously to the polymerization mixture at the start of the process. Preferred non-vinyl crosslinkers include hexane diamine, glycerin, ethylene glycol diglycidyl ether, ethylene glycol diacetate, polyethylene glycol 400, polyethylene glycol 600, and polyethylene glycol 1000. Examples of more preferred non-vinyl crosslinkers include polyethylene glycol 400 and polyethylene glycol 600. Mixtures of non-vinyl crosslinkers can be employed.

The dimodal crosslinkers that can be employed in the process of this invention are agents that have at least one polymerizable vinyl group and at least one functional group capable of reacting with carboxyl groups. To distinguish these from normal vinyl crosslinkers, we call them "dimodal crosslinkers," because they use two different modes of reaction to form a crosslink. Examples of dimodal crosslinkers include hydroxyethyl methacrylate, polyethylene glycol monomethacrylate, glycidyl methacrylate, and allyl glycidyl ether. Many examples of these type of agents are given in U.S. Pat. Nos. 4,962,172 and 5,147,956 which teach the manufacture of absorbent films and fibers by (1) the preparation of linear copolymers of acrylic acid and hydroxyl containing monomers, (2) forming solutions of these copolymers into the desired shapes, and (3) fixing the shape by heating the polymer to form ester crosslinks between the pendant hydroxyl and carboxyl groups. In the current invention the dimodal crosslinkers advantageously are added homogeneously to the polymerization mixture at the start of the process. Preferred dimodal crosslinkers include hydroxyethyl (meth)acrylate, polyethylene glycol 400 monomethacrylate, glycidyl methacrylate. Hydroxyethyl (meth)acrylate is an example of a more preferred dimodal crosslinker. Mixtures of dimodal crosslinkers can be employed.

Combinations of crosslinkers can be employed. The total amount of all crosslinkers present is sufficient to provide a polymer with good absorptive capacity, good absorption under load, and a low percent of extractable materials. Preferably the crosslinkers are present in an amount of 1,000 parts per million or more by weight based on the amount of the polymerizable monomer present, more preferably 2,000 ppm or more and most preferably 4000 ppm or greater. Preferably, the crosslinkers are present in an amount of 50,000 parts per million or less by weight based upon the amount of the polymerizable monomer present, more preferably in amounts of 20,000 ppm or less and most preferably 15,000 ppm or less.

In those embodiments of the invention that utilize a blend of polyvinyl crosslinkers with non-vinyl and or dimodal crosslinkers, the effect on heat-treated capacity of all three types of crosslinkers is additive in nature. That is, if the amount of one crosslinker is increased the amount of another must be decreased to maintain the same overall heat-treated capacity. In addition, the proportion of the crosslinker components within the blend may be varied to achieve different polymer properties and processing characteristics. In particular the polyvinyl crosslinkers are typically more expensive than non-vinyl or dimodal crosslinkers. Therefore, the overall cost of the polymer is reduced if a greater proportion of the crosslinker blend is composed of less expensive non-vinyl and or dimodal crosslinkers. However, the non-vinyl and dimodal crosslinkers function essentially as latent crosslinkers. That is, the crosslinking imparted to the polymer by these agents is essentially not developed or seen until after a heat-treatment step. Little if any toughness is added to the hydrogel immediately after polymerization by use of such latent crosslinkers. This is an important concern for those processes for which a "tough" gel is desirable.

If too little of the total crosslinker blend is composed of polyvinyl crosslinker the polymerized hydrogel may not have sufficient toughness to be easily ground, processed, and dried. For this reason the proportion of polyvinyl crosslinker in the total crosslinker blend is preferably at least sufficient to produce a hydrogel that has enough toughness to be readily ground, processed, and dried. This toughness is inversely proportional to the centrifuged capacity of the polymer after drying but before heat-treatment. The exact amount of polyvinyl crosslinker required in the blend to achieve this level of toughness will vary, but is enough to provide a centrifuged absorption capacity of the polymer after drying but before heat-treatment of at least 10 g/g and preferably 45 g/g or less, more preferably 40 g/g or less, and most preferably 35 g/g or less.

Conventional additives that are well known in the art, such as surfactants, may be incorporated into the polymerization mixture. Polymerization can be accomplished under polymerization conditions in an aqueous or nonaqueous polymerization medium or in a mixed aqueous/nonaqueous polymerization medium. Polymerization accomplished by processes which employ nonaqueous polymerization media may use various inert hydrophobic liquids which are not miscible with water, such as hydrocarbons and substituted hydrocarbons including halogenated hydrocarbons as well as liquid hydrocarbons having from 4 to 20 carbon atoms per molecule including aromatic and aliphatic hydrocarbons, as well as mixtures of any of the aforementioned media.

In one embodiment, the polymer particles are prepared by contacting the monomers and crosslinkers of the invention in an aqueous medium in the presence of a free radical or oxidation reduction (redox) catalyst system and optionally a chlorine- or bromine-containing oxidizing agent under conditions such that a crosslinked hydrophilic polymer is prepared. As used herein, the term "aqueous medium" means water, or water in admixture with a water-miscible solvent. Such water-miscible solvents include lower alcohols and alkylene glycols. Preferably the aqueous medium is water.

The monomers and crosslinkers are preferably dissolved, dispersed or suspended in a suitable polymerization medium such as, for example, the aqueous medium, at a concentration level of 15 percent by weight or greater, more preferably 25 percent or greater, and most preferably 29 percent or greater. The monomers and crosslinkers are preferably dissolved, dispersed or suspended in the aqueous medium.

Another component of the aqueous medium used to prepare the superabsorbent polymers comprises a free radical initiator, which may be any conventional water soluble polymerization initiator including, for example, peroxygen compounds such as sodium, potassium and ammonium peroxodisulfates, caprylyl peroxide, benzoyl peroxide, hydrogen peroxide, cumene hydroperoxide, tertiary butyl diperphthalate, tertiary butyl perbenzoate, sodiumperacetate and sodiumpercarbonate. Conventional redox initiator systems can also be utilized, which are formed by combining the foregoing peroxygen compounds with reducing agents, such as, for example, sodium bisulfite, sodium thiosulphate, L- or iso-ascorbic acid or a salt thereof or ferrous salts. The initiator can comprise up to 5 mole percent based on the total moles of polymerizable monomer present. More preferably the initiator comprises from 0.001 to 0.5 mole percent based on the total moles of polymerizable monomer in the aqueous medium Mixtures of initiators can be employed.

In one embodiment of the invention, at least one chlorine- or bromine-containing oxidizing agent is added to the monomer mixture or to the wet hydrogel in order to reduce the amount of residual monomers in the final polymer. It is preferably added to the monomer mixture. Preferred oxidizing agents are bromates, chlorates and chlorites. Preferably a chlorate or bromate salt is added. The counterion of the bromate or chlorate salt can be any counterion which does not significantly interfere in the preparation of the polymers or their performance. Preferably, the counterions are alkaline earth metals ions or alkali metal ions. More preferred counterions are the alkali metals, with potassium and sodium being even more preferred. Chlorine-containing oxidizing agents are preferred. The oxidizing agent is present in sufficient amount such that after heat-treatment the residual monomer level is reduced and the desired balance of centrifuged absorption capacity and absorption under load (AUL) is achieved.

The chlorine- or bromine-containing oxidizing agent is present in a sufficient amount such that after heat-treatment the desired balance of polymer properties is achieved. If too much of the oxidizing agent is used, the ultimate properties of the polymers are degraded. If an insufficient amount is added, the above-described property improvements do not occur and the absorptive capacity will be low. Preferably, 10 ppm by weight or greater of a chlorine- or bromine-containing oxidizing agent based on the total weight of monomers (a), (b) and (c) is added, more preferably 50 ppm or greater and even more preferably 100 ppm or greater and most preferably 200 ppm or greater. Desirably, the amount of a chlorine- or bromine-containing oxidizing agent added is 2000 ppm or less by weight based on the monomers, more desirably 1000 ppm or less, preferably 800 ppm or less and most preferably 500 or less.

The process of the invention may be performed in a batch manner wherein all of the reaction materials are contacted and the reaction proceeds, or it may take place with the continuous addition of one or more of the components during the reaction period. The polymerization mixture in the polymerization medium is subjected to polymerization conditions that are sufficient to produce the water-absorbent polymers. Preferably, the reaction is performed under an inert gas atmosphere, for example, under nitrogen or argon. The reaction may be performed at any temperature at which polymerization occurs, preferably 0° C. or greater, more preferably 25° C. or greater and most preferably 50° C. or greater. The reaction is conducted for a time sufficient to result in the desired conversion of monomer to crosslinked hydrophilic polymer. Preferably, the conversion is 85 percent or greater, more preferably 95 percent or greater and most preferably 98 percent or greater. Advantageously, initiation of the reaction occurs at a temperature of at least 0° C.

It is also possible to prepare the polymer of the current invention with the addition of recycled "fines" to the polymerization mixture. See U.S. Pat. No. 5,342,899. The amount of fines added to the polymerization mixture is preferably less than 12 weight percent based on the amount of monomer in the polymerization mixture, more preferably less than 10 weight percent, and most preferably less than 8 weight percent.

It is also possible to carry out the polymerization process using multiphase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. Polymerization occurs in the aqueous phase, and suspensions or emulsions of this aqueous phase in an organic solvent permit better control of the exothermic heat of polymerization and further provide the flexibility of adding one or more of the aqueous reaction mixture components in a controlled manner to the organic phase.

Inverse suspension polymerization procedures are described in greater detail in Obayashi et al., U.S. Pat. No. 4,340,706; Flesher et. al. U.S. Pat. No. 4,506,052; and Stanley et al. U.S. Pat. No. 5,744,564. When inverse suspension polymerization or inverse emulsion polymerization techniques are employed, additional ingredients such as surfactants, emulsifiers and polymerization stabilizers may be added to the overall polymerization mixture. When any process employing organic solvent is utilized, it is important that the hydrogel-forming polymer material recovered from such processes be treated to remove substantially all of the excess organic solvent. Preferably, the hydrogel-forming polymers contain no more than 0.5 percent by weight of residual organic solvent.

During polymerization, the polymer of the invention generally absorbs all of the aqueous reaction medium to form a hydrogel. The polymer is removed from the reactor in the form of an aqueous hydrogel. The term "hydrogel" as used herein refers to water swollen superabsorbent polymer or polymer particles. In preferred embodiments, hydrogels coming out of the reactor comprise 15 to 50 percent by weight polymer, with the remainder comprising water. In a more preferred embodiment the hydrogel comprises 25 to 45 percent polymer. The hydrogel is preferably processed into a particulate shape during the polymerization reaction process in the reactor by the agitator to facilitate the removal of the hydrogel from the reactor. Preferred particle sizes of the hydrogel range from 0.001 to 25 cm, more preferably from 0.05 to 10 cm. In multiphase polymerization, the superabsorbent polymer hydrogel particles may be recovered from the reaction medium by azeotropic distillation and/or filtration followed by drying. If recovered by filtration, then some means of removing the solvents present in the hydrogel must be used. Such means are commonly known in the art.

The polymer of the invention may be in the form of particles or other forms, such as fibers.

After removal from the reactor, the hydrogel polymer is subjected to comminution, such as, for example, by a convenient mechanical means of particle size reduction, such as grinding, chopping, cutting or extrusion. The size of the gel particles after particle size reduction should be such that homogeneous drying of the particles can occur. Preferred particle sizes of the hydrogel range from 0.5 to 3 mm. This particle size reduction can be performed by any means known in the art that gives the desired result. Preferably, the particle size reduction is performed by extruding the hydrogel.

In another embodiment the solution comprising silver complex ions is added to the crosslinked wet hydrogel prior to or after comminution and it is preferably sprayed onto the gel. The silver complex ions are then distributed substantially uniformly throughout the superabsorbent polymer particles rather than concentrated on the surfaces.

The comminuted hydrogel polymer particles are subjected to drying conditions to remove the remaining polymerization medium and any dispersing liquid including the optional solvent and substantially all of the water. Desirably, the moisture content of the polymer after drying to remove the polymerization medium and any dispersing liquid including the optional solvent and substantially all of the water is between zero and 20 weight percent, preferably between 5 and 10 weight percent.

The temperature at which the drying takes place is a temperature high enough such that the polymerization medium and liquid including water and optional solvent is removed in a reasonable time period, yet not so high so as to cause degradation of the polymer particles, such as by breaking of the crosslink bonds in the polymer. Preferably, the drying temperature is 180° C. or less. Desirably, the temperature during drying is 100° C. or above, preferably 120° C. or above and more preferably 150° C. or above. The drying time should be sufficient to remove substantially all of the water and optional solvent. Preferably, a minimum time for drying is 10 minutes or greater, with 15 minutes or greater being preferred. Preferably, the drying time is 60 minutes or less, with 25 minutes or less being more preferred. In a preferred embodiment, drying is performed under conditions such that water, and optional solvent, volatilizing away from the absorbent polymer particles is removed. This can be achieved by the use of vacuum techniques or by passing inert gases or air over or through the layers of polymer particles. In a preferred embodiment, the drying occurs in dryers in which heated air is blown through or over layers of the polymer particles. Preferred dryers are fluidized beds or belt dryers. Alternatively a drum dryer may be used. Alternatively the water may be removed by azeotropic distillation. Such techniques are well known in the art.

During drying, the superabsorbent polymer particles may form agglomerates and may then be subjected to comminution, such as, for example, by mechanical means for breaking up the agglomerates. In a preferred embodiment, the superabsorbent polymer particles are subjected to mechanical particle reduction means. Such means can include chopping, cutting and/or grinding. The object is to reduce the particle size of the polymer particles to a particle size acceptable in the ultimate end use. In a preferred embodiment, the polymer particles are chopped and then ground. The final particle size is preferably 2 mm or less, more preferably 0.8 mm or less. Preferably the particles have a size of 0.01 mm or greater, more preferably 0.05 mm or greater. Dried superabsorbent polymer particles of the present invention can be used as the basis polymer for further surface crosslinking treatment, for example, using polyvalent cations like aluminum ions and/or using one of the crosslinkers mentioned above by coating and subsequent heating at elevated temperatures.

In one embodiment of the invention, the polymer particles are subjected to a heat-treatment step after drying and optional particle size reduction. Heat-treatment of the polymer provides a beneficial increase in the absorption under load (AUL) of the superabsorbent polymer, particularly the AUL under higher pressures. Suitable devices for heat-treatment include, but are not limited to, rotating disc dryers, fluid bed dryers, infrared dryers, agitated trough dryers, paddle dryers, vortex dryers, and disc dryers. One of ordinary skill in the art would vary the time and temperature of heat-treatment as appropriate for the heat transfer properties of the particular equipment used.

The time period and temperature of the heat-treatment step are chosen such that the absorption properties of the polymer are improved as desired. The polymers are desirably heat-treated at a temperature of 170° C. or above, more desirably 180° C. or above, preferably at 200° C. or above and most preferably at 220° C. or above. Below 170° C. no improvement in the absorption properties is seen. The temperature should not be so high as to cause the polymers to degrade. Preferably, the temperature is 250° C. or below and more preferably 235° C. or below. The polymers are heated to the desired heat-treatment temperature and preferably maintained at such temperature for 1 minute or more and more preferably 5 minutes or more and most preferably 10 minutes or more. Below 1 minute no improvement in properties is generally seen. If the heating time is too long it becomes uneconomical and there is a risk that the polymer may be damaged. Preferably polymer particles are maintained at the desired temperature for 60 minutes or less, preferably 40 minutes or less. Above 60 minutes no significant improvement in properties is noticed. The properties of the polymer particles can be adjusted and tailored by adjustment of the temperature and the time of the heating step.

After heat-treatment the polymer particles may be difficult to handle due to static electricity. It may be desirable to rehumidify the particles to reduce or eliminate the effect of the static electricity. Methods of humidification of dry polymers are well known in the art. In a preferred mode, the dry particles are contacted with water vapor. The dry particles are contacted with a sufficient amount of water to reduce or eliminate the effects of the static electricity, yet not so much so as to cause the particles to agglomerate. Preferably, the dry particles are humidified with 0.3 percent or more by weight of water and more preferably 5 percent or more by weight of water. Preferably, the dry particles are humidified with 10 percent or less by weight of water and more preferably 6 percent or less by weight of water. Optionally, agglomeration prevention or rehydration additives may be added to the crosslinked hydrophilic polymer. Such additives are well known in the art and include surfactants and inert inorganic particles such as silica; see, for example, U.S. Pat. Nos. 4,286,082 and 4,734,478; and DE 2706135. Remoisturization can also be accomplished using certain salt solutions as taught in EP 0 979 250.

According to the process of this invention for the preparation of superabsorbent polymers with odor control properties the silver complex ions preferably are added to the process in a solution. The silver complex ions are advantageously added in an amount providing 1 to 100,000 ppm silver in the final polymers. The concentration of the silver complex ion in the solution is not critical. Desirable concentrations of the silver complex ions in water range from 0.01 to 20 weight percent. The amount of solution comprising the silver complex ions preferably ranges from 0.1 to 10 weight percent, more preferably from 1 to 6 weight percent, based on dry polymer.

The silver complex ions may be added to the polymerization mixture (i) during polymerization or prior to the beginning of the polymerization, or (ii) to the crosslinked hydrogel prior to or after comminution, or (iii) to the dried polymer particles prior to or after heat-treatment, if a heat-treatment is performed. It is also within the scope of the present invention to add the silver complex ions several times at various stages of the preparation process. It is preferred to add the solution comprising silver complex ions to the dried polymer particles, which are optionally heat-treated. The silver complex ions are then distributed on and adsorbed to the polymer particle surfaces because their migration into the inner particle region is limited. Additional mixing means, such as agitating and stirring, may be applied to improve the distribution of the silver complex ions on the surfaces of the polymer particles. The silver complex ions located on the polymer particle surfaces can be released when contacted with liquids, such as bacteria infected urine, and this is an economical use of odor controlling agents.

If the aqueous solution comprising silver complex ions is added to the dried and optionally heat-treated polymer the solution may additionally contain a dust control agent, for example a propoxylated polyol as described in U.S. Pat. Nos. 6,323,252 and 5,994,440. The propoxylated polyols are particularly suitable to bind the fine dust of the final superabsorbent polymer particles without causing agglomeration, and to bind the fine particles of powdery additives on the surface. The addition of the propoxylated polyol further results in a more homogeneous distribution of the silver complex ions or other aqueous additives on the surface of the superabsorbent polymer particles in the absence of organic solvent. Exemplary propoxylated polyols are available from The Dow Chemical Company under the brand name VORANOL. The propoxylated polyol is advantageously used in an amount of from 500 to 2,500 ppm, based on the weight of dry polymer. The concentration of the propoxylated polyol in water preferably ranges from 1 to 10 weight percent and more preferably from 3 to 6 weight percent.

In one embodiment the dried and optionally heat-treated polymer particles are surface treated with aluminum sulfate. The aluminum sulfate may be added as an aqueous solution prior to or after the addition of the silver complex ions or the aluminum sulfate may be added to the aqueous solution comprising silver complex ions and thus applied to the polymer together with the silver complex ions. The aluminum sulfate is preferably used in an amount of from 0.1 to 10 weight percent, based on dry polymer and its concentration in water is desirably from 5 to 49 weight percent. The use of an aqueous solution comprising silver complex ions and both a propoxylated polyol and aluminum sulfate is especially preferred.

Other additives of carrier type or non-carrier type to which some odor control function is attributed may be used in addition to the silver complex ions. The additional additives may be added to the dried and optionally heat-treated polymer prior to, simultaneously with or after the addition of silver complex ions. Exemplary additives are activated carbon, chlorophyllin, chelating agents, soda, sodium bicarbonate, copper sulfate, copper acetate, zinc sulfate, silicates, clay, cyclodextrin, citric acid, chitosan, ion exchange resin particles or combinations thereof. Polycationic polymers such as, for example, poly(diallyldimethylammonium chloride) of different molecular weights may be used for better adsorption of the anionic silver complex ions on the superabsorbent polymer particle surfaces. Zeolites may be also used in addition to the silver complex ions. Natural or synthetic zeolites may be used as carriers in the non-treated form or after pretreatment with the silver complex ions, for example, by incorporating silver complex ions in the pores of the zeolite. Optionally, polycationic polymers, such as for example, poly(diallyldimethylammonium chloride) may be also used for better adsorption when the zeolite particles are used with superabsorbent polymer particles. When zeolite or other powdered additives are used, the polycationic poly (diallyldimethylammonium chloride) may increase the binding between superabsorbent polymer particle surfaces and the fine particles, which results in lower dust development.

To increase the flowability of the dried and optionally heat-treated polymer particles silicon dioxide, preferably famed silica, or other fine inorganic or organic powders may be mixed with the polymer particles. Powdery additives are desirably added to and mixed with the polymer particles together with the famed silica. The fumed silica is preferably used in amounts of from 0.01 to 5 weight percent, and more preferably from 0.05 to 3 weight percent, all based on dry polymer. An exemplary fumed silica is Aerosil R972, available from Degussa AG, Germany. The additives may be added dry or in dispersed form, such as in the form of an aqueous dispersion.

In yet another embodiment, dried and optionally heat-treated silver-free polymers are combined with silver-treated superabsorbent polymer. The silver-treated superabsorbent polymer can be normally-sized material or can be "fines" or mixture of these. "Fines" are superabsorbent polymer particles that are created from drying, grinding, and natural attrition during transport and heat-treating process of the typical gel process. The fine particle size fraction is in general undesirably small and therefore not suitable for incorporation in personal care article such as diapers, as described in U.S. Pat. No. 5,342,899. This fine particle size fraction is often small enough to create dusting problems in production and a source of performance deterioration due to the well-known gel blocking tendency upon initial wetting. In a preferred embodiment, silver treated 'fines' are superabsorbent polymer particles which preferably pass through a 45 mesh (350 µm) screen and have been optionally heated to a temperature of from 170 to 250° C. for from 1 to 60 minutes prior to the addition of silver complex ions in solution as described above.

The water-absorbent polymer particles of this invention can be used in any use wherein absorption and binding of aqueous fluids is desired and is especially suitable for such applications where it would be desirable to inhibit the development of malodor. In a preferred embodiment, the superabsorbent polymer particles of this invention are mixed into or attached to a structure of absorbent material such as synthetic or natural fibers or paper-based woven or nonwoven fibers to form a structure. In such a structure the woven or nonwoven structure functions as a mechanism for wicking and transporting fluid via capillary action to the superabsorbent polymer particles which bind and retain such fluids. Examples of such structures are sanitary napkins, diapers, and adult incontinence structures. In addition, there are various applications of the superabsorbent polymers with odor control property in non-personal care applications, for example, in medical care, agriculture, horticulture, gardening, pet litter, fertilizer, packaging and food packaging.

The absorbent structures according to the present invention comprise means to contain the superabsorbent polymer particles having odor control property. Any mean capable of containing the described superabsorbent polymer particles, which means is further capable of being positioned in a device such as an absorbent garment, is suitable for use in the present invention. Many such containment means are known to those skilled in the art. For example, the containment means may comprise a fibrous matrix such as an airlaid or wetlaid web of cellulosic fibers, a meltblown web of synthetic polymeric fibers, a spunbonded web of synthetic polymeric fibers, a coformed matrix comprising cellulosic fibers and fibers formed from a synthetic polymeric material, airlaid heat-fused webs of synthetic polymeric material or open-celled foams. In one embodiment, it is preferred that the fibrous matrix comprise less than 10, preferably less than 5, weight percent of cellulosic fibers. Further, the containment means may comprise a support structure, such as a polymeric film, on which the superabsorbent polymer particles is affixed. The superabsorbent polymer particles may be affixed to one or both sides of the support structure which may be water-pervious or water-impervious.

The absorbent structures according to the present invention are suited to absorb many fluids including body fluids such as, for example, urine, menses, and blood and are suited for use in absorbent garments such as diapers, adult incontinent products and bed pads; in catamenial devices such as sanitary napkins and tampons; and in other absorbent products such as, for example, wipes, bibs and wound dressings. Accordingly, in another aspect, the present invention relates to an absorbent garment comprising an absorbent structure as described above.

In yet another aspect, the present invention relates to an absorbent structure described above but with treatment of silver complex ions in a solution without superabsorbent polymer particles. The silver solution of this invention may be sprayed or impregnated to one or more structures of the absorbent articles mentioned above. Such structures, though not containing superabsorbent polymer particles, may be also used in different applications such as adult incontinence structures, diapers, sanitary napkins, packaging, food packaging, and medical care such as wound dressing.

Specific Embodiments of the Invention

The following examples are included to illustrate the invention, and do not limit the scope of the claims. All parts and percentages are by weight unless otherwise stated.

Test Methods

Method for Microbiological Evaluation

Preparation of Bacterial Strain Suspensions

The following analytical grade components were added to a vessel and stirred for 15 minutes to make 10 kg of synthetic urine solution:
200 g urea
90 g NaCl
11.0 g $Mg_2SO_4 \cdot 7H_2O$
7.95 g $CaCl_2 \cdot 2H_2O$
9691.0 g distilled water A synthetic urine medium that simulates real urine in which various bacteria strains can proliferate was developed for use in these experiments. Peptone (tryptone soya broth (Oxoid Company, UK)) was found to be useful as a nutrition medium for bacteria proliferation in the synthetic urine solution.

A peptone solution was prepared by dissolving 60 g of tryptone soya broth powder (product code: CM 129, Oxoid company, UK) in 1000 g distilled water with thorough mixing. The solution was then sterilized by autoclaving at 121° C. for 20 minutes.

A culture medium was prepared by adding 4 g of the peptone solution to 400 g of synthetic urine solution in a 1000 ml Erlenmeyer flask prior to the start of culture growth; this corresponds to a peptone concentration of 0.60 g in 1000 g synthetic urine. The culture medium was inoculated with 2–3 bacterial colonies from Columbia sheep blood (5 percent) agar plates (Becton Dickinson) which had been kept at 4° C. not longer than 1 week. In the case of *Proteus mirabilis* an approximately equivalent amount of bacteria was used.

To start culture growth, each flask containing an inoculated culture medium at 49° C. was placed into an incubator at 38° C. It took about 14 hours for the temperature of the inoculated culture medium to rise to 38° C.

The following bacteria strains were employed: *Escherichia coli* (hereinafter EC), an ATC 25922 (American Tissue Type Culture Collection) type strain; *Proteus mirabilis* (hereinafter PM) (ATTC 14153); and *Klebsiella pneumoniae* (hereinafter KP) (ATTC 10031). For the tests conducted below, each cultured strain was used either as a single bacteria strain suspension, or was mixed with suspensions of the other 2 strains to make a mixture having an equal volume of each of the three suspensions. The mixture of suspensions had a total bacterial content approximately equal to the total bacterial content of a single strain suspension. The CFU (colony forming unit) of the cultures was then determined by viable plate counts.

CFU (Colony Forming Unit) Analysis

Polymer samples having a particle size fraction between 100 to 800 pm were used for CFU analysis unless otherwise stated. The CFU count was determined using the following procedure. 5.00 g of each polymer sample were placed into a 500 ml glass bottle containing 150 ml of the single or the mixed bacteria strain suspension (PM, EC, KP). The mixture of polymer and bacteria suspension was then stirred (100 rpm) using a dumb-bell shaped magnetic stirrer having length of 5 cm until the stirring was stopped by swelling polymer gels (time zero). 1 g of the swollen gel was taken and was placed into a small plastic tube with a screw cap. 10 ml of 0.9 percent NaCl solution were added to the tube, followed by immediate, vigorous shaking of the tube. Using 0.9 percent sodium chloride solution, the supernatant was then used for a further series of dilution, for example, the final dilution of 1,000 and 10,000 fold, wherein the dilution with 10 ml of 0.9 percent sodium chloride solution above was included. Unless otherwise stated, the CFU results were those obtained from the 10,000 fold dilution. For better comparison, in some cases the result of the 1,000 fold dilution was restandardized to that for the 10,000 fold dilution which results in CFU numbers being smaller than 1.25 µl of each diluted solution were put onto a plate, and CFUs were counted after incubation for 24 h at 38° C. The CFU analysis was performed 0, 4 and 24 h after time zero. In all experiments, the samples of the present invention were analyzed for CFU together with the pure bacteria suspension and a control polymer sample. The CFU analysis was performed in duplicate, and the arithmetic mean was taken in all cases.

Sniff Test

A single, experienced laboratory technician did the sniff test. Bacteria-inoculated gel samples were prepared by mixing 5 g polymer with 150 ml of the inoculated culture medium prepared above. The sniff test was performed using bacteria-inoculated gel samples after incubation of the polymer for 24 hours at 38° C. The following ratings were used for describing the odor of the polymer gels.

TABLE 1

Degrees of Sniff Test Results

| Degree | Odor Description |
|---|---|
| +++ | Very Strong ammonia odor, very strongly malodorous |
| ++ | Strong ammonia odor, strongly malodorous |
| + | Ammonia odor, malodorous |
| 0 | Non ammonia odor, non malodorous |

Polymer A

Polymer A is DRYTECH S230R brand superabsorbent polymer which is commercially available from Dow Deutschland GmbH & Co. OHG. It had a degree of neutralization of 68 mol percent. It had a particle size fraction between 100 and 800 μm.

Preparation of Silver Complex Solutions

Silver Thiosulfato Complex

Complexation of silver chloride salt using thiosulfate was done at room temperature. An excess of thiosulfate was used in order to make silver thiosulfato complex. The desired amount of sodium thiosulfate pentahydrate (STP) salt was weighed in a 100 mL glass bottle. 36 g of water were then added and the solution was stirred with a magnetic stirrer. Silver chloride was then added to the solution with agitation. The bottle was closed and the solution was stirred for about 5 minutes at room temperature.

Silver Chloro Complex 13 g of sodium chloride were dissolved in 60 g of water. This solution was heated to 95° C. in a water bath under the agitation of a magnetic stirrer. 0.1596 g of silver chloride was added to the solution. After 5 minutes in the water bath, 1 g of NaCl was added if the silver salt was not dissolved; this procedure was repeated until the silver salt was dissolved.

Sample Preparation Procedure

The following procedure was employed for all experiments except as otherwise noted.

Dry Polymer A powder (1.2 kg) was placed at room temperature into a 5 liter laboratory scale blender (Loedige Company, Germany). Fumed silica (3.0 g) (AEROSIL R972, available from Degussa-Huels Company, Germany) was added to the polymer powder to increase flowability. When other powder additives, for example, cyclodextrin, activated carbon, chlorophyllin, etc. were used, they were added to the mixture of the polymer and famed silica. The blender contents were then blended for 15 minutes.

The required amount of water-soluble salt or other water-soluble additive, was dissolved in a mixture of 36 g of deionized water and 1.14 g of VORANOL CP 755 brand propoxylated polyol (VORANOL is a trademark of The Dow Chemical Company). The resulting aqueous fluid was then sprayed directly into the Loedige blender during agitation (126 rpm) and the whole mixture was blended for a further 15 minutes before unloading. The CFU (Colony Forming Unit) Analysis, as described hereinabove, was then performed using the mixed bacteria strain suspension.

The silver ion concentrations in all following tables were based on dry polymer. In all of the following experiments the "control" sample was the corresponding inoculated polymer without an odor control additive. Experiments having the designation "-0" represent the bacterial suspension with neither polymer nor additives. All examples marked as * are comparative experiments and are not examples of the present invention.

Experiment Series 1

The Sample Preparation Procedure was followed using silver thiosulfato complex solutions prepared by dissolving varying amounts of silver chloride and sodium thiosulfate pentahydrate ("STP") as described above.

TABLE 2

Addition of Various Amounts of Silver Thiosulfato Complex Ions - CFU Counts for Various Polymers using a Mixture of Bacteria Strains Suspension (PM, EC, KP)

| Sample | Time | CFU | Odor |
|---|---|---|---|
| Ex 1-0 Bacteria Strain Suspension (Mixture of PM, EC, and KP)* | 0 h | 57 | +++ |
|  | 4 h | 82 |  |
|  | 24 h | 41 |  |
| Control 1* | 0 h | 60.5 | ++ |
|  | 4 h | 119.5 |  |
|  | 24 h | 150 |  |
| Ex 1-1 100 ppm $Ag^+$ = 0.1596 g AgCl/0.83 g STP | 0 h | 59 | 0 |
|  | 4 h | 9.2 |  |
|  | 24 h | 0.6 |  |
| Ex 1-2 300 ppm $Ag^+$ = 0.4788 g AgCl/1.66 g STP | 0 h | 42 | 0 |
|  | 4 h | 11.2 |  |
|  | 24 h | 0.4 |  |

The CFU results clearly show that silver thiosulfato complex ions were very effective for odor control via antibacterial effects. The sniff test results also showed clearly reduced malodor as compared to the control.

Experiment Series 2

The Sample Preparation Procedure was followed using silver chloro complex solutions prepared by dissolving varying amounts of silver chloride and sodium chloride in excess as described above.

TABLE 3

Addition of Silver Chloride Complex Ions - CFU Counts for Various Polymers using a Mixture of the Bacteria Strains Suspension (PM, EC, KP)

| Sample | Time | CFU | Odor |
|---|---|---|---|
| Ex 2-0 Bacteria Strain Suspension (Mixture of PM, EC and KP)* | 0 h | 130 | +++ |
|  | 4 h | 120.5 |  |
|  | 24 h | 39.5 |  |
| Control 2* | 0 h | 200 | ++ |
|  | 4 h | 172 |  |
|  | 24 h | 164 |  |
| Ex 2-1 100 ppm $Ag^+$ = 0.1596 g AgCl/21 g NaCl | 0 h | 169.5 | 0 |
|  | 4 h | 0.1 |  |
|  | 24 h | 0 |  |

The results clearly show that silver chloro complex ions also control odor via antibacterial effects as can be seen in the CFU and sniff test.

Experiment Series 3

In Example 3-1 AGRICOLITE zeolite was used in addition to the silver thiosulfato complex ions. AGRICOLITE is a natural occurring zeolite which is a potassium sodium aluminosilicate of the clinoptilolite type. AGRICOLITE zeolite material having a particle size distribution of from 0 to 100 μm was obtained by sieving AGRICOLITE zeolite material having a particle size distribution of from 0 to 0.5 mm. The zeolite (0–100 μm) was dried in an air-forced lab oven at 190° C. for 3 h, and cooled down to room temperature in the desiccator. The zeolite was further ground and sieved again using a 100 µm sieve.

The Sample Preparation Procedure was followed using silver thiosulfato complex solution.

TABLE 4

Addition of Silver thiosulfato Complex Ions and Zeolite Powder - CFU Counts for Various Polymers using a Mixture of bacteria Strains Suspension (PM, EC, KP)

| Sample | Time | CFU | Odor |
|---|---|---|---|
| Ex 3-0 Bacteria Strain Suspension | 0 h | 96.5 | +++ |
| (Mixture of PM, EC and KP)* | 4 h | 123 | |
|  | 24 h | 75.5 | |
| Control 3* | 0 h | 118.5 | ++ |
|  | 4 h | 168 | |
|  | 24 h | 157 | |
| Ex 3-1 | 0 h | 70 | 0 |
| 100 ppm Ag$^+$ = 0.1596 g AgCl/0.9 g | 4 h | 2 | |
| STP and 24 g Agricolite | 24 h | 0 | |

It was seen that the superabsorbent polymer of the present invention treated with silver thiosulfato complex ions combined with zeolite were very effective for odor control.

What is claimed is:

1. A process for the preparation of water-absorbent, water insoluble polymer particles, the process comprising: (I) polymerizing a polymerization mixture comprising: (a) one or more ethylenically unsaturated carboxyl-containing monomers, (b) one or more crossliniking agents, (c) optionally one or more comonomers copolymerizable with the carboxyl-containing monomer, and (d) a polymerization medium, to form a crosslinked hydrogel, (II) comminuting the hydrogel to particles, and (III) drying the hydrogel, wherein a solution comprising silver complex ions is added to the dried polymer particles, and wherein the dried polymer particles from step (III) are treated with an aqueous solution of aluminum sulfate prior to, simultaneously with or after the addition of the solution comprising silver complex ions.

2. The process of claim 1 wherein the silver complex ions are silver chloro complex ions or silver thiosulfato complex ions or mixtures thereof.

3. The process of claim 1 wherein the silver complex ions are added in an amount providing 1 to 10,000 ppm silver cations, based on weight of dry polymer.

4. The process of claim 1 wherein the dried polymer particles from step (III) are (IV) heated to a temperature of from 170 to 250° C. for from 1 to 60 minutes prior to or after addition of the silver complex ions.

5. The process of claim 1 wherein the solution comprising silver complex ions is an aqueous solution.

6. The process of claim 5 wherein the aqueous solution comprising silver complex ions additionally comprises a polyether polyol.

7. The process of claim 1 wherein fumed silica is mixed with the dried polymer particles from step (III) prior to or simultaneously with the addition of the solution comprising silver complex ions.

8. The process of claim 1 further comprising addition of an additive selected from the group consisting or activated carbon, chlorophyllin, chelating agents, soda, sodium bicarbonate, copper sulfate, copper acetate, zinc sulfate, silicates, clay, cyclodextrin, citric acid, chitosan, ion exchange resin particles, polycationic polymers, poly(diallyldimethylammonium chloride), zeolites or combinations thereof, prior to, simultaneously with or after the addition of the solution comprising silver complex ions.

* * * * *

UNITED STATES PATENT AND TRADEMARK OFFICE
CERTIFICATE OF CORRECTION

PATENT NO. : 7,183,345 B2 Page 1 of 1
APPLICATION NO. : 10/471874
DATED : February 27, 2007
INVENTOR(S) : Young-Sam Kim It is certified that error appears in the above-identified patent and that said Letters Patent is hereby corrected as shown below:

Title page,
Item (86), "PCT/US02/20872" should read -- PCT/US02/20572 --.

Column 1,
Line 9, "PCT/US02/20872" should read -- PCT/US02/20572 --.

Column 3,
Line 39, "and (II) drying" should read -- and (III) drying --.

Column 5,
Line 64, "alkaline metal ammo-" should read -- alkaline metal, ammo- --.

Column 9,
Line 25, "medium Mixtures of" should read -- medium. Mixtures of --.

Column 14,
Line 20, "famed silica," should read -- fumed silica, --.
Line 23 "famed silica" should read -- fumed silica --.

Column 17,
Line 52, "famed silica" should read -- fumed silica --.

Signed and Sealed this

Eighth Day of July, 2008

JON W. DUDAS
*Director of the United States Patent and Trademark Office*